United States Patent [19]

Reabe et al.

[11] 4,302,403
[45] Nov. 24, 1981

[54] PROCESS FOR REACTING SULFURIC ACID AND AN AROMATIC HYDROCARBON TO PURIFY A DISULFONIC ACID PRODUCT OF AN AROMATIC HYDROCARBON

[75] Inventors: Kenneth G. Reabe, Delmont; Hans Dressler, Monroeville; Frederick M. Covelli, Murrysville, all of Pa.

[73] Assignee: Koppers Company, Inc., Pittsburgh, Pa.

[21] Appl. No.: 171,450

[22] Filed: Jul. 23, 1980

Related U.S. Application Data

[63] Continuation of Ser. No. 30,597, Apr. 16, 1979, abandoned, and a continuation of Ser. No. 848,788, Nov. 7, 1977, abandoned, which is a continuation of Ser. No. 695,578, Jun. 14, 1976, abandoned.

[51] Int. Cl.$^3$ ............................................. C07C 143/24
[52] U.S. Cl. ................................................. 260/505 E
[58] Field of Search ........................ 260/505 E, 505 C

[56] References Cited

U.S. PATENT DOCUMENTS

| | | | |
|---|---|---|---|
| 1,227,252 | 5/1917 | Dennis | 260/505 |
| 1,848,883 | 3/1932 | Hill | 260/505 |
| 2,379,585 | 7/1945 | Maguire | 260/505 |
| 3,636,090 | 1/1972 | Luecken | 260/505 |

*Primary Examiner*—Alan Siegel
*Attorney, Agent, or Firm*—Oscar B. Brumback; Herbert J. Zeh, Jr.; J. Timothy Keane

[57] ABSTRACT

Unreacted sulfuric acid contained in a disulfonic acid product of an aromatic hydrocarbon that is produced from the reaction of the aromatic hydrocarbon or the mono-sulfonic acid of the aromatic hydrocarbon with a strong sulfonating agent is removed from the disulfonic acid product by reacting the sulfuric acid with additional aromatic hydrocarbon to produce the mono-sulfonic acid of the aromatic compound. The disulfonic acid product of the aromatic hydrocarbon containing sulfuric acid is reacted with the aromatic hydrocarbon at a molar ratio of aromatic hydrocarbon to sulfuric acid in the range of about 0.25 to around 2 and at a temperature in the range of 130° to 200° C. to obviate the need to remove any water formed during the course of the reaction.

5 Claims, No Drawings

PROCESS FOR REACTING SULFURIC ACID AND AN AROMATIC HYDROCARBON TO PURIFY A DISULFONIC ACID PRODUCT OF AN AROMATIC HYDROCARBON

CROSS-REFERENCE TO RELATED APPLICATIONS

This is a continuation of application Ser. No. 30,597, filed Apr. 16, 1979, now abandoned, and a continuation of Ser. No. 848788 filed Nov. 7, 1977, now abandoned, which is a continuation of Ser. No. 695578, filed June 14, 1976, now abandoned.

BACKGROUND OF THE INVENTION

This invention relates to the production of sulfonated aromatic hydrocarbons. More particularly, this invention relates to an improvement in the process for producing a disulfonic acid of an aromatic hydrocarbon and a mono-sulfonic acid of an aromatic hydrocarbon.

Benzene disulfonic acid is prepared with good yields by reacting benzene or mono-sulfonated benzene with an excess amount of inhibited fuming sulfuric acid (oleum). The benzene disulfonic acid product contains only a small amount of water produced from the sulfonation reaction but it does contain unreacted, sulfuric acid along with by-products such as benzene mono-sulfonic acid, other sulfonated acids of benzene, sulfones, and other by-products. The separation of the unreacted sulfuric acid from the disulfonated benzene at the completion of the reaction is difficult and expensive.

One method of separating the unreacted sulfuric acid from the benzene disulfonic acid is described in Canadian Pat. No. 784,253 by John O'Brochta entitled, "Process for Separation of Sulfonated Benzenes". This patent discloses separating the unreacted sulfuric acid from benzene disulfonic acid in a benzene disulfonic acid product by passing the product as a film of 0.5 to 3.0 millimeters through an evaporation zone at a pressure of less than 0.10 mm of mercury and at a temperature of 200°–240° C. In an alternative embodiment, the product is reacted with benzene to convert any unreacted sulfuric acid to benzene mono-sulfonic acid. The water formed during this reaction is continuously removed by formation of a water-benzene azeotrope which is distilled from the reaction. The benzene mono-sulfonic acid is separated from the benzene disulfonic acid in the evaporation zone.

In the above-described process the water formed from the reaction of the unreacted sulfuric acid in the benzene disulfonic acid product was continuously removed to enable the reaction to go to completion. This is done on the theory that if the water is not eliminated from the reaction, the water formed by the reaction would dilute the concentration of sulfuric acid. This dilution would cause the rate of reaction to decrease until a limiting concentration of sulfuric acid is reached and the reaction stops. This dilution effect is common in a sulfonation reaction of an aromatic compound with sulfuric acid.

Several methods have been developed to overcome the dilution effect of the water formed during the course of a sulfonation reaction where sulfuric acid is used as the sulfonating agent. These methods include physically removing the water from the reaction or chemically combining the water to lessen its effect on the reaction. In the above-described process the water of reaction was removed by the formation of a benzene-water azeotrope which involves the use of more benzene than that needed to react with the unreacted sulfuric acid. This operation is time-consuming and increases the cost of the process. Also, this operation leads to an increase in the production of sulfone by-products.

The primary objective of the improvement of the present invention is to provide a process for reacting any unreacted sulfuric acid sulfonating agent present in a disulfonic acid product produced by reaction of an aromatic hydrocarbon and a strong sulfonating agent with the aromatic hydrocarbon to produce the monosulfonic acid of the aromatic hydrocarbon without the need for removing the water formed during the course of the reaction.

SUMMARY OF THE INVENTION

The present invention is an improvement in the step of reacting an aromatic hydrocarbon with unreacted sulfuric acid in the disulfonic acid product of the aromatic hydrocarbon which is produced by reacting the aromatic hydrocarbon or the mono-sulfonated aromatic hydrocarbon with a strong sulfonating agent. It is this reaction of the unreacted sulfuric acid with the aromatic hydrocarbon while any water formed from the reaction is continuously removed in order to obtain a good conversion to the sulfonated aromatic hydrocarbon that the present invention is primarily concerned.

In the description of this invention the term aromatic hydrocarbon includes benzene; alkylated benzenes, like toluene and xylenes; and naphthalene. Also the phrase disulfonic acid product of the aromatic hydrocarbon includes the disulfonic acid of the aromatic hydrocarbon along with the mono-sulfonic acid of the aromatic hydrocarbon, unreacted sulfuric acid, aromatic hydrocarbon, other sulfonated acids of the aromatic hydrocarbon and sulfones. Also, the term strong sulfonating agent encompasses those sulfonating agents that react with the aromatic hydrocarbon to produce a substantial amount of the disulfonic acid of the aromatic hydrocarbon like 65% oleum or any fuming sulfuric acid mixture having a free $SO_3$ concentration greater than 20 weight percent. This strong sulfonating agent may be in a stoichiometric molar amount with the aromatic hydrocarbon or in an excess amount.

The improvement of the present invention is based on the discovery that in the presence of the large amounts of the strongly acidic disulfonic acid of an aromatic hydrocarbon present in a disulfonic acid product of the aromatic hydrocarbon the water formed by the reaction between the unreacted sulfuric acid in the disulfonic acid product of the aromatic hydrocarbon and added aromatic hydrocarbon need not be removed from the reaction in order to obtain good conversions to monosulfonated aromatic hydrocarbon.

The improvement in such reaction comprises: reacting the unreacted sulfuric acid in a disulfonic acid product of an aromatic hydrocarbon with the aromatic hydrocarbon in a molar ratio of the aromatic hydrocarbon to unreacted sulfuric acid in the range of about 0.25 to around 2 and at a temperature in the range of about 130 to about 200° C. at atmospheric pressure. The unreacted sulfuric acid contained in the disulfonic acid product of the aromatic hydrocarbon is obtained from the reaction of the aromatic hydrocarbon or the monosulfonated aromatic hydrocarbon with a strong sulfonating agent (excess amount of oleum). The sulfur trioxide in the oleum preferentially reacts with the aromatic hydrocarbon or the mono-sulfonic acid of the aromatic hydrocarbon to produce the disulfonic acid of the aromatic hydrocarbon and some mono-sulfonic acid of the aromatic hydrocarbon. The sulfuric acid in the oleum reacts to a small extent with the aromatic hydrocarbon to produce the mono-sulfonic acid of the aromatic hydrocarbon, but to a great extent remains unreacted and is present in the disulfonic acid product of the aromatic hydrocarbon.

The improvement of this invention may be conducted in a batch operation or a continuous operation and the aromatic hydrocarbon reacted with the unreacted sulfuric acid may be in a liquid or vapor state. The pressure may be atmospheric pressure or superatmospheric pressure or subatmospheric pressure with a corresponding change in the reaction temperature range.

DETAILED DESCRIPTION OF THE INVENTION

When one disulfonic acid product of an aromatic hydrocarbon is used in the process of this invention that particular aromatic hydrocarbon or another aromatic hydrocarbon may be used in the process. For example, if disulfonic acid product of the aromatic hydrocarbon is a benzene disulfonic acid product, then either benzene or toluene can be reacted with the unreacted sulfuric acid in a benzene disulfonic acid product. The process of the invention is conducted in essentially the same manner regardless of the specific aromatic hydrocarbon used. Minor changes may be necessary to accommodate for the different molecular weights of the various aromatic hydrocarbons but these changes are within the ability of one skilled in the art. When the aromatic hydrocarbon is naphthalene, which is a liquid at the operating conditions, liquid or solid naphthalene may be added directly to the reaction. Since naphthalene has a boiling point around 218° C. and the operating conditions of the reaction are in the range of about 130° C. to around 200° C., the naphthalene can not be reacted in the vapor state; whereas benzene and the alkylated benzenes can be reacted in the liquid or vapor state. In general except for the above mentioned variations the process described below is the same for each of the aromatic hydrocarbons.

The process of this invention can be used generally in the reaction of the aromatic hydrocarbon with sulfuric acid to produce the mono-sulfonated aromatic hydrocarbon. In this operation it would not be necessary to remove the water formed by the reaction of the aromatic hydrocarbon and the sulfuric acid in order to take the reaction to completion. This is accomplished by the process of this invention where the aromatic hydrocarbon and sulfuric acid are reacted in a molar ratio of the aromatic hydrocarbon to sulfuric acid in the range of about 0.25 to around 2 and at a temperature in the range of 130° C. to 200° C. in the presence of a disulfonic acid product containing at least 20 weight percent disulfonic acid.

The concentration of the sulfonating agent is very important when sulfonating an aromatic hydrocarbon with sulfuric acid. It is known that when sulfuric acid is employed as the sulfonating agent the sulfonation reaction stops at a definite $H_2SO_4$ concentration. The sulfonation reaction can be expressed as:

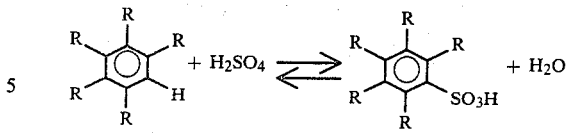

where R is hydrogen or an alkyl group with one to three carbon atoms. The limiting concentration of $H_2SO_4$ is expressed by the Greek letter $\pi$. An example of the limiting concentration is in the production of benzenesulfonic acid where sulfonation stops regardless of temperature or agitation when the value of $\pi$ is 64 percent, corresponding to the hydrate $H_2SO_4 \cdot 1.5H_2O$. In practice, no action takes place after the acidity reaches 66.4 percent $H_2SO_4$. Many procedures have therefore been devised and employed to eliminate the water of reaction as it is formed to force the equilibrium reaction depicted in the above formula to the right.

Now we have found that in the presence of a disulfonic acid product having a substantial amount, at least 20 weight percent, of the disulfonic acid of the aromatic hydrocarbon, and at particular conditions of molar ratio and temperature the aromatic hydrocarbon and sulfuric acid can be reacted without removing the water of reaction.

The process of this invention is preferably used to purify a benzene meta-disulfonic acid product containing unreacted sulfuric acid. The benzene meta-disulfonic acid product must have a sufficient purity to be used for the production of resorcinol by the caustic fusion process. The advantage of using a benzene meta-disulfonic acid product with no or a low content of sulfuric acid is that the sodium salt of the benzene meta-disulfonic acid will not contain sodium sulfate which would cause complications in the caustic fusion reaction. In the preferred process of this invention the aromatic hydrocarbon is benzene and the disulfonic acid of the aromatic hydrocarbon is meta-benzene disulfonic acid.

Benzene or mono-sulfonated benzene or a mixture of the two compounds may be reacted with oleum, and especially 65% oleum, in any manner known to those skilled in the art in order to produce the benzene meta-disulfonic acid product. A sulfone inhibitor, for example, an alkali metal sulfate compound, may be added to the reaction to reduce sulfone formation. The benzene meta-disulfonic acid product, hereinafter referred to as "diacid", contains mostly benzene meta-disulfonic acid. The diacid also contains unreacted sulfuric acid along with by-products such as benzene para-disulfonic acid, benzene mono-sulfonic acid, diphenyl sulfone, sulfonated diphenyl sulfones, and any sulfone inhibitor, if one was added to the reaction. An example of a typical analysis of a diacid is the following: 62% by weight benzene meta-disulfonic acid, 28.4% by weight sulfuric acid, and 9.6% by weight by-products.

The diacid which preferably contains at least about 20 percent meta-benzene disulfonic acid is contacted with benzene either in a liquid or vapor state. The amount of benzene which contacts the diacid is that which gives a molar ratio of benzene to sulfuric acid in the range of about 0.25 to around 2. This contacting is performed at a temperature in the range of 130° to 200° C. and preferably in the range of 130° to 180° C., at atmospheric pressure so that the sulfuric acid in the diacid reacts with the benzene to produce benzene mono-sulfonic acid. If the molar ratio of benzene to unreacted sulfuric acid in the diacid is below a molar ratio of about 0.25, only a small amount of the sulfuric acid will be converted to benzene mono-sulfonic acid, therefore leaving some sulfuric acid in the diacid. If the molar ratio of benzene to unreacted sulfuric acid is increased to higher than around 2, all the sulfuric acid will be converted to benzene mono-sulfonic acid but unreacted benzene will remain. This unreacted benzene could be separated from the reacted diacid and recycled to the diacid containing sulfuric acid. Such an operation would be time-consuming and expensive, particularly so if the excess benzene formed an azeotrope with any water that may be present. Also, any large excesses of benzene lead to the production of tarry by-products. The temperature range is critical. If the temperature is below 130° C. at atmospheric pressure, the reaction rate of the reaction between the sulfuric acid in the diacid and the benzene would be impractical. If the temperature exceeds 180° C., there is some loss of benzene meta-disulfonic acid and a production of some tarry materials. If the temperature exceeds 200° C., the benzene meta-disulfonic acid in the diacid undergoes desulfonation and resulfonation, thereby decreasing the quantity of benzene meta-disulfonic acid and increasing the quantity of sulfone and other by-products.

The reacted diacid, which refers to the diacid which has been contacted with benzene at the above conditions, contains mostly benzene meta-disulfonic acid with an increased amount of benzene mono-sulfonic acid over that of an unreacted diacid along with other by-products, but little if any sulfuric acid. This reacted diacid may be treated further with oleum or free sulfur trioxide to convert the increased amount of benzene mono-sulfonic acid to benzene meta-disulfonic acid. This benzene meta-disulfonic acid may be used for the caustic fusion production of resorcinol. The reacted diacid may also be used directly for the caustic fusion production of resorcinol and phenol. Also, the reacted diacid may be subjected to a separation step to separate the benzene meta-disulfonic acid from the benzene mono-sulfonic acid which may be treated separately in a caustic fusion process to produce resorcinol and phenol.

The improvement of this invention may be performed in a batch or continuous operation. A continuous operation may be conducted in a cascade-overflow-type system by charging diacid, which is preferably molten, and benzene to a reaction vessel. The benzene may be in either the liquid or vapor state. The reaction occurs in the reaction vessel and the product, i.e., reacted diacid, overflows into a second vessel. This second vessel may be a collecting vessel or another reaction vessel or a series of reaction vessels, if most of the sulfuric acid in the diacid was not reacted in the first reaction vessel. In these additional vessels more benzene may be added to assure conversion of cost of the sulfuric acid to benzene mono-sulfonic acid.

The improvement of this invention is illustrated by the following examples.

EXAMPLE I

Benzene is an amount of 117.2 grams (1.50 moles) was added in 35 minutes at 140°–150° C. to 1000 grams of diacid containing 211.0 grams (2.15 moles) of $H_2SO_4$ is a well-stirred, 1000 ml kettle. Reaction was rapid and no difficulty was encountered in holding reaction temperature. The conversion to benzene mono-sulfonic acid was 67% based on sulfuric acid and 96% based on benzene fed which was 0.7 mole of benzene per mole of sulfuric acid.

This example is presented in Table I as Example I along with the conditions and results of other batch examples.

TABLE I

| Example No. | Reactants Contained $H_2SO_4$ (moles) | Benzene (moles) | Mole[a] Ratio | Time (Min) | Temp. (°C.) | Products BSA Wt. % | $H_2SO_4$ Wt. % | Conversion[b] % |
|---|---|---|---|---|---|---|---|---|
| 1[c] | 2.15 | 1.50 | 0.7/1 | 35 | 140–150 | 20.1 | 6.6 | 67 |
| 2[c] | 0.34 | 0.34 | 1/1 | 265 | 130–150 | 23.4 | 2.5 | 78 |
| 3[c] | 0.34 | 0.37 | 1.1/1 | 170 | 135–155 | 27.5 | 3.1 | 92 |
| 4[c] | 0.34 | 0.43 | 1.25/1 | 260 | 135–155 | 29.4 | 0.9 | 98 |
| 5[c] | 0.11 | 0.11 | 1/1 | 55 | 140–150 | 26.8 | 2.9 | 89 |
| 6[c] | 0.12 | 0.12 | 1/1 | 45 | 170–180 | 27.4 | 0.3 | 91 |
| 7[d] | 0.43 | 0.22 | 0.62/1 | 125 | 60–145 | 15.5 | 9.8 | 62 |
| 8[d] | 0.4 | 0.4 | 1/1 | 110 | 130–150 | 26.8 | 3.6 | 80 |
| 9[d] | 0.12 | 0.12 | 1/1 | 135 | 85–150 | 26.5 | 1.9 | 77 |

[a]Mole ratio of benzene to contained sulfuric acid.
[b]Based on sulfuric acid.
[c]Initial diacid contained 0% BSA (mono-sulfonated benzene), 58.2% MBDSA (meta-benzene disulfonic acid), 21.1% sulfuric acid and 17.0% other compounds including sodium sulfate as a sulfone inhibitor.
[d]Initial diacid contained 0% BSA, 64.5% MBDSA, 24.5% $H_2SO_4$, and 11.4% other compounds including sodium sulfate as a sulfone inhibitor.

EXAMPLE II

Continuous operation was conducted in a cascade-overflow-type system with two stirred, 1000 ml flasks. Molten diacid and liquid benzene were pumped into the first reactor. The product overflowed into the second stirred reactor, where additional liquid benzene was added. The product from the second reactor overflowed to a collection vessel.

The first reactor was charged with 403.0 grams (245 ml) of diacid which contained less than 0.5 wt. % benzene mono-sulfonic acid, 58.2 wt. % meta-benzene disulfonic acid, 21.1% sulfuric acid, and 18.0 wt. % of other by-product compounds including sodium sulfate as a sulfone inhibitor. An amount of molten diacid, 840.1 grams, was charged to a graduated funnel. The diacid in the reactor was heated to 150° C. and benzene was added at ca. 2 ml/min. under the surface of the stirred mass. Benzene (180 ml total) was fed to the reactor for 75 minutes at 145°–150° C. before the addition of molten diacid from the graduated addition funnel was begun at 3–4 grams/minute. After an additional 80 minutes, product began overflowing into the second reactor, which was maintained at 160°–170° C. The level was allowed to build up for 45 minutes before the addition of benzene (2 ml/min.) was begun in the second reactor. After an additional 60 minutes, overflow began from the second reactor to the collection vessel. The reaction was continued until all of the diacid had been fed to the first reactor.

Samples were taken from the first reactor, the second reactor, and from the collection vessel. The samples were quenched with water and extracted with methylene chloride and the extracts and aqueous solutions were analyzed. The results of the analysis and other data are tabulated in Table II.

TABLE II

| Reactors | Feed (gm) Diacid | Feed (gm) Benzene | Temperature °C. | Recovered Samples Wt. (g) | Products BSA Wt. % | Products $H_2SO_4$ Wt. % | Products Benzene Wt. % | Products Other[a] Wt. % | % Conversion to BSA |
|---|---|---|---|---|---|---|---|---|---|
| Reactor 1 | 1,243.1 gm | 466.4 g | 145–150 | 738.4 | 24.9 | 3.9 | 0.52 | 69.4 | 83% |
| Reactor 2 | — | 137.3 g | 160–170 | 579.0 | 31.8 | 0.0 | 0.19 | 69.3 | 100% |
| Collection Vessel | — | — | — | 111.6 | 31.4 | 0.0 | 0.27 | 66.9 | 100% |

[a]Includes mostly MBDSA, with minor amounts of PBDSA (para-benzene disulfonic acid), diphenyl sulfone, and sodium sulfate.
Total reaction time was 315 minutes.

According to the provisions of the patent statutes we have explained the principle, preferred construction and mode of operation of our invention and have described what we now consider to represent its best embodiment. However, we desire to have it understood that within the scope of the appended claims the invention may be practiced otherwise than as specifically described.

We claim:

1. A chemical purification process for removing unreacted sulfuric acid from a meta-benzene disulfonic acid product, which product is useful in the caustic fusion method of making resorcinol, the meta-benzene disulfonic acid product produced by reacting benzene or benzene monosulfonic acid with an excess of oleum, said purification process comprising:
   (a) providing a mixture containing at least about 20 percent by weight of meta-benzene disulfonic acid and an amount of unreacted sulfuric acid;
   (b) adding benzene to said mixture in an amount providing a molar ratio of said benzene to said unreacted sulfuric acid in said mixture in a range from about 0.25 to one to about 2 to one;
   (c) maintaining the temperature of said mixture in a range from about 130° C. to about 200° C. during the reaction of said benzene and said unreacted sulfuric acid;
   (d) allowing the reaction to proceed without removing water formed during reaction of said benzene and said unreacted sulfuric acid;
whereby there is produced purified meta-benzene disulfonic acid having little or no unreacted sulfuric acid.

2. The process of claim 1 wherein the reaction temperature is in the range from about 130° C. to about 180° C.

3. The process of claim 1 wherein said benzene added to said mixture is in a liquid state.

4. The process of claim 1 wherein said benzene added to said mixture is in a vapor state.

5. The process of claim 1 wherein benzene sulfonic acid is distilled from the meta-benzene disulfonic acid product.

* * * * *